United States Patent [19]

Ralls et al.

[11] Patent Number: 5,741,659
[45] Date of Patent: Apr. 21, 1998

[54] RAPID MICROBIAL PROTEASE ASSAY

[75] Inventors: Stephen Alden Ralls, Great Lakes; Lloyd Grant Simonson, Deerfield; Sylvia Zottu Schade, Riverside, all of Ill.

[73] Assignee: The United States of America as represented by the Secretary of the Navy, Washington, D.C.

[21] Appl. No.: 583,170

[22] Filed: Jan. 4, 1996

[51] Int. Cl.$^6$ .............................. C12Q 1/37; C12Q 1/04; C12Q 1/52; A01N 37/18

[52] U.S. Cl. .............................. 435/23; 435/24; 435/34; 435/16; 435/13; 435/25; 435/4; 514/2; 514/70; 514/740; 564/305

[58] Field of Search .................... 435/23, 24, 34, 435/16, 13, 25, 4; 514/2, 70, 740; 436/74; 564/305

[56] References Cited

U.S. PATENT DOCUMENTS

| | | | |
|---|---|---|---|
| 4,457,866 | 7/1984 | Karges et al. | 435/4 |
| 4,480,029 | 10/1984 | Dolana | 435/13 |
| 4,588,836 | 5/1986 | Matsumoto et al. | 435/16 |
| 4,675,290 | 6/1987 | Matsumoto et al. | 435/16 |
| 4,877,727 | 10/1989 | Miike et al. | 435/25 |

OTHER PUBLICATIONS

Pederson et al; "Microbios", vol. 63, pp. 165–171, 1990.

Jenzano et al; "Archives of Oral Biology;" vol. 33(9); pp. 641–644; 1988.

*Primary Examiner*—Louise Leary
*Attorney, Agent, or Firm*—A. D. Spevack; W. Garuert

[57] ABSTRACT

An assay for detecting microbial protease activity in clinical and laboratory samples is described which comprises gathering a sample suspected of containing certain microorganisms having the desired protease activity; immobilizing the microorganisms in the sample on a solid phase substrate; contacting the immobilized microorganisms with an enzymatic substrate producing an enzymatic substrate end-product; contacting the enzymatic substrate end-product with a chemical enhancing reagent producing a detectable chromogenic reaction which varies in intensity with the level of protease activity in the sample; and detecting the chromogenic reaction whereby the semi-quantitative presence of the protease activity in the sample is determined. The device for conducting these assays is a frame or support which holds a solid phase substrate capable of binding the sought microorganisms of interest while permitting drainage of other materials or fluids, which may contain host proteases, away from the immobilized microorganisms.

8 Claims, 1 Drawing Sheet

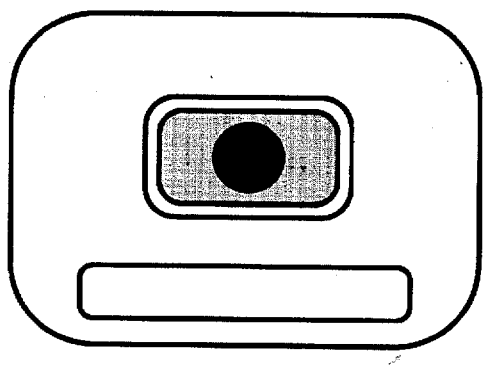
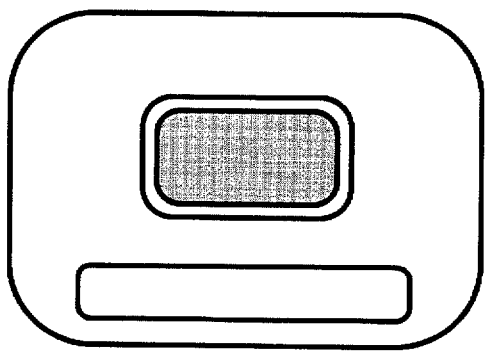
FIG 1                    FIG 2

RAPID MICROBIAL PROTEASE ASSAY

BACKGROUND OF THE INVENTION

1. Field of the Invention

This invention relates to a rapid assay means and method for detecting microbial proteases in dental plaque, saliva, oral rinse samples and other clinical and laboratory specimens and samples. More specifically, this invention relates to detecting activity of microbial proteases, e.g., chymotrypsin-like proteases, trypsin-like proteases or collagenases, on a whole-mouth basis or at specific sites within a mouth thereby assisting in the diagnosis of periodontal disease; assessing risk for developing periodontal disease; planning treatment for periodontal disease; and monitoring the efficacy of periodontal treatment.

2. Description of the Prior Art

Periodontal disease is one of the most common afflictions affecting mankind and is widely accepted to have a bacterial etiology. Periodontal disease is the most common cause of tooth loss in adults. Within this invention, the term periodontal disease encompasses all inflammatory diseases affecting the supporting structures of the teeth and having a bacterial etiological component including, for example, but not limited to, gingivitis, necrotizing ulcerative gingivitis, adult periodontitis, localized juvenile periodontitis, rapidly progressive periodontitis, refractory periodontitis, and pre-pubertal periodontitis. Also within this invention, the term plaque refers to the primarily bacterial mass which accumulates over time in either subgingival or supragingival locations and which is associated with periodontal disease. Also within this invention the terms active and activity refer to proteases that possess the ability to react with enzymatic substrates such as described herein, e.g., para-nitroanilide peptide substrates and para-nitroanilide amino acid substrates for microbial proteases.

Periodontal disease is usually characterized by one or more of the following: tissue inflammation, bleeding on periodontal probing, attachment loss, bone loss, suppuration, mobility, pain, and, ultimately, tooth loss. Certain species of oral bacteria have been associated with periodontal disease, including spirochetes (1). Spirochetes are frequently the most numerous bacteria found in periodontally diseased areas in both adults (1–4) and children (5). Oral spirochetes from the genus *Treponema* form a significant segment of the subgingival plaque in humans with periodontal disease and can be as much as 50% of the detectable microbial cells (2). *Treponema denticola* appears to be the spirochete species most frequently associated with diseased periodontal sites (2,3). Spirochetes have been shown to increase in number in periodontal disease and decrease after treatment (3). Simonson et al. have shown that the numbers of *Treponema denticola* in dental plaque increase in direct proportion to the severity of periodontal disease (6). Besides spirochetes, other prominent bacterial species associated with periodontal disease include *Fusobacterium nucleatum, Eikenella corrodens, Capnocytophaga* spp., *Porphyromonas gingivalis, Prevotella intermedia* and *Campylobacter rectus*, among others.

Trypsin-like proteases, chymotrypsin-like proteases and collagenases are proteases associated with several important bacterial species implicated in periodontal disease (1–3, 7–13). Trypsin-like proteases are associated with *Treponema denticola* and *Porphyromonas gingivalis* (1,7–13); chymotrypsin-like proteases are associated with *Treponema denticola* and *Capnocytophaga* spp. (1–3). Within this invention, the term trypsin includes trypsin-like proteases and the term chymotrypsin includes chymotrypsin-like proteases such as have been described (2,3,7–13). This assay provides a rapid method and means for detecting microbial proteases in plaque, saliva and oral rinse samples and thereby serves to assist in the diagnosis, risk assessment, treatment planning and monitoring of treatment efficacy for periodontal disease. This assay can also be used to assist in the identification of microorganisms in culture and in other clinical and laboratory specimens and samples by determining enzyme activity.

The use of succinyl-alanyl-alanyl-prolyl-phenylalanyl-para-nitroanilide (SAAPFpNA) and other para-nitroanilide amino acid and para-nitroanilide peptide substrates for microbial proteases, separately or in combination, has not been reported as part of a rapid, chairside assay for microbial proteases as described herein. No simple, rapid assays for microbial proteases have been reported although several parallel, but substantially unrelated, inventions have been described. The detection of proteases as described in this invention assists in the diagnosis, risk assessment, treatment planning and treatment monitoring of periodontal disease in a manner faster, simpler and less expensive than any currently described. Rosenberg et al. in U.S. Pat. No. 4,976,951 filed Aug. 28, 1985, have described DENTAL CARIES DIAGNOSTIC AND LOCALIZATION TECHNIQUE; this method, however, is substantially different than the invention described herein. Ebersole has described a SEROLOGICAL METHOD FOR THE IDENTIFICATION OF MICROORGANISMS in U.S. Pat. No. 4,458,014 filed Jan. 11, 1982, specifically for the identification of diseases of the mouth. Chen et al. have described in U.S. Pat. No. 4,866,167 filed Aug. 26, 1985 a DETECTION OF HUMAN ORAL CELLS BY NUCLEIC ACID HYBRIDIZATION to detect bacterial species including *Streptococcus mutans*. The methods of both Ebersole and Chen et al. are technically complex, time consuming and are not rapid. Ralls and Simonson in U.S. patent application Ser. No. 08/508,653, filed Jul. 28, 1995, now pending have described a RAPID IMMUNOASSAY FOR CARIOGENIC BACTERIA; in U.S. patent application Ser. No. 08/562,772, filed Nov. 27, 1995, pending have described a RAPID IMMUNOASSAY TO DETECT ANTIBODIES IN SALIVA TO DISEASE-RELATED ANTIGENS. These inventions are immunodiagnostic assays based on antigen-antibody reactions and are substantially different in concept to the invention described herein.

There are no simple methods reported to rapidly detect microbial protease activity in plaque, saliva, oral rinse samples and other clinical and laboratory specimens and samples. Conventional clinical diagnostic and risk assessment methods for periodontal disease are not based on bacterial profiles, rather they usually rely on subjective clinical data. As such, it is often a clinical dilemma to distinguish periodontally diseased sites which are actively breaking down from quiescent or even treated sites. Conventional methods are often considered too slow or inaccurate for screening purposes and are often fraught with errors of interpretation. This is particularly true when dentists are seeking immediate answers for patients in their care and for persons who are traveling to distant locations where dental services are difficult to obtain. What is needed is a rapid, simple-to-operate assay to detect ongoing protease activity in plaque, saliva or oral rinse samples which, in turn, allows an estimation of the specific periodontopathic bacterial species involved. An inexpensive test is needed that can be developed and read in less than an hour, preferably in five minutes or less, which can assist in screening patients or specific sites for the diagnosis of periodontal disease; monitoring patients or sites for risk of developing periodontal disease; planning treatment for periodontal disease; and monitoring patients or sites for the efficacy of periodontal treatment.

SUMMARY OF THE INVENTION

Accordingly, an object of this invention is an assay means and method for rapidly detecting the presence of active microbial proteases in dental plaque, saliva or oral rinse samples.

Another object of this invention is an assay means and method to rapidly assist in the diagnosis of periodontal disease and the determination of periodontal disease activity (positive for certain levels of protease activity) on a whole mouth basis or at specific sites within a mouth.

A further object of this invention is an assay means and method to rapidly assist in assessing risk for developing periodontal disease on a whole mouth screening basis or at specific sites within a mouth.

A further object of this invention is an assay means and method to rapidly assist in planning treatment for patients with periodontal disease.

An additional object of this invention is an assay means and method to rapidly assist in monitoring the efficacy of periodontal treatment on a whole mouth screening basis or at specific sites within a mouth.

An additional object of this invention is an assay means and method to rapidly assist in the determination of specific protease activity useful in the identification of microorganisms.

An additional object of this invention is an assay means and method to rapidly assist in the identification of active microbial proteases in other clinical and laboratory specimens and samples such as urine, sweat, tears, blood, serum, stool, gastric fluid, synovial fluid and phlegm.

An additional object of this invention is a device for conducting the rapid assay.

These and additional objects of the invention are accomplished by an assay for detecting microbial protease activity comprising gathering a plaque, saliva, oral rinse sample or other clinical or laboratory sample suspected of containing the desired protease, spotting the sample on a solid phase substrate, washing the sample with phosphate-buffered saline and contacting the sample with an enzymatic substrate such as SAAPFpNA or some other para-nitroanilide peptide or para- nitroanilide amino acid substrate for microbial protease activity. A chromogenic reaction develops following the addition of a para-dimethylaminocinnamaldehyde chemical enhancing reagent in samples positive for proteases specific for the para-nitroanilide substrate chosen. The reaction is semi-quantitative wherein the intensity of the reaction is proportional to the level of microbial protease activity present in the sample. The device for conducting these assays is a frame or support which holds a solid phase substrate capable of immobilizing or retaining microorganisms of interest while permitting drainage of other materials and fluids through and away from the microorganisms.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1 is an embodiment of the device for the method and illustrates a positive reaction and the presence of chymotrypsin-like activity.

FIG. 2 is an embodiment of the device for the method and illustrates a negative reaction and the absence of chymotrypsin-like activity.

DESCRIPTION OF THE PREFERRED EMBODIMENTS

The invention is directed toward a rapid assay to detect microbial protease activity in plaque, saliva or oral rinse samples as well as in other clinical and laboratory specimens and samples. Microbial proteases are associated with bacterial species implicated in the etiology of periodontal disease, e.g., trypsin and chymotrypsin with *Treponema denticola* and trypsin with *Porphyromonas gingivalis*. The detection of microbial proteases in plaque, saliva or oral rinse samples indicates the presence in the samples of the certain bacteria which produce the proteases, e.g., *Treponema denticola*, *Treponema socranskii* and *Capnocytophaga* spp. with chymotrypsin. The invention can be used for both site-specific and whole mouth applications, including assisting in the diagnosis, risk assessment, treatment planning and monitoring treatment efficacy for periodontal disease. This rapid assay method for determining the presence of proteases in oral clinical samples is fully developed and readable in under an hour, usually about five minutes or less. Within this invention, the term rapid assay is an assay or test that can be developed in under an hour, preferably in less than one-half hour. Most preferably, this assay is fully readable in approximately five minutes or less from the application of the patient's dental plaque, saliva or oral rinse sample to the device. The method and equipment are inexpensive and technically easy to use.

As mentioned, periodontal disease is one of the most prevalent diseases to affect mankind and is the most common cause of tooth loss in adults. By using saliva, pooled plaque or oral rinse samples, this invention can rapidly screen patients for microbial protease levels associated with specific bacterial species thereby indicating the general nature of the host's resident bacterial plaque population. This information, in turn, can assist in the diagnosis, risk assessment, treatment planning and monitoring efficacy of treatment for periodontal disease. By using plaque from specific sites, similar information can be determined on a site basis. The invention is planned as a cornerstone of an institutional periodontal disease diagnosis and risk assessment program. The value of this invention in a risk assessment program is that by knowing risk for developing periodontal disease, treatment resources can be directed in the most effective and efficient manner. The primary advantages of this invention include: 1) microbial protease activity correlates highly with both periodontal disease severity and the bacterial species associated with periodontal disease; 2) the assay allows simple and unique differentiation between host and microbial proteases; 3) the assay can be performed and read in about five minutes; 4) the assay is inexpensive; and 5) the assay is simple, technically easy to use and easily performed by auxiliary personnel. The method can be used in a dental operatory with definitive results obtained while the patient is still in the chair.

In general, the invention is an assay means and method which uses a simple, semi-quantitative chromogenic reaction to detect microbial protease activity. For periodontal disease, the method comprises gathering a sample suspected of containing the oral bacteria of interest from a patient. The sample can be gathered from patients by any of the known techniques for gathering dental plaque, saliva or oral rinse samples. Samples are usually used undiluted but can be incorporated into suitable sample media. An aliquot of the sample or sample-containing media is placed on a solid phase substrate, preferably a flow-through filter type device (such as marketed by Devaron, Inc., Dayton, N.J.) or a device such as described by Oprandy in U.S. Pat. No. 5,039,493 filed May 4, 1990. The microorganisms present are immobilized on the filter surface of the solid phase substrate primarily by mechanical retention and the substrate is washed with phosphate-buffered saline. The solid phase substrate can be any of the commonly used substrates such as nitrocellulose filter media or any of the materials described by Oprandy. Once the microorganisms in the unknown sample are immobilized on the solid phase substrate and washed, the filter surface is contacted with SAAPFpNA or some other para-nitroanilide peptide substrate or para-nitroanilide amino acid substrate for microbial proteases producing an enzymatic substrate end-product. The enzymatic substrate end-product on the filter surface is then contacted with a para-dimethylaminocinnamaldehyde reagent, producing an enhanced chromogenic reaction specific for microbial protease activity. Although some proteases such as chymotrypsin can be contributed by the host in blood, serum or gingival crevicular fluid, the host protease-containing fluids, if present, pass through the substrate filter surface generally leaving only the immobilized protease-containing microorganisms to react. Once labeled, the amount of the protease activity in the sample can be semi-quantified by assessing the relative strength of the color development produced as a result of the chromogenic reaction.

The invention can have alternative embodiments. While the invention is described primarily to detect microbial proteases of an oral origin, the device, with little if any modification, can be used to detect microbial protease activity in other clinical and laboratory specimens and samples such as urine, sweat, tears, blood, serum, stool, gastric fluid, synovial fluid, phlegm and microbial cultures. In an another alternative embodiment, combinations of enzymatic substrates can be used to detect multiple microbial protease activities. Similarly, combinations of different chemical enhancing reagents can be used that react with these combinations of enzymatic substrates. In an additional alternative embodiment, the solid phase substrate device can be pre-blocked with a suitable blocking agent to further minimize the retention of host proteases on the filter surface of the device. Additionally, the solid phase substrate does not have to precisely assume the form described herein. Maintaining the same general concept, the invention can be easily modified as a "dip stick" or other similar technique.

Having described the invention, the following example is given to illustrate specific applications of the invention for detecting chymotrypsin, including the best mode now known to perform the invention. This specific example is not intended to limit the scope of the invention described in this application.

EXAMPLE

An assay for chymotrypsin-like activity in plaque, saliva or oral rinse samples is described in four simple and rapid steps:

1. Five µl of an undiluted saliva (or oral rinse) sample are spotted onto a solid phase substrate flow-through filter device (Devaron, Inc., Dayton, N.J., 0.45 µm). Alternatively, a clinical sample of human dental plaque, either from a specific site or pooled from several sites within the same mouth, is collected in sterile phosphate-buffered saline (PBS), pH 7.4, and 5 µl of suspension are spotted onto the filter device. In either case, fluids are allowed to drain through the filter surface. The PBS solution, pH 7.4, is prepared as follows:

| PBS, pH 7.4 | 1 L |
| --- | --- |
| Distilled water | 1000 ml |
| NaCl | 8.0 g |
| $KH_2PO_4$ | 0.2 g |
| $Na_2HPO_4 \cdot 12H_2O$ | 2.9 g |
| KCl | 0.2 g |
| $NaN_3$ | 0.2 g |

2. The spotted filter device surface is washed by adding 1 drop (50 µl) of PBS to the filter surface and letting it drain through.

3. A succinyl-alanyl-alanyl-prolyl-phenylalanyl-para-nitroanilide (SAAPFpNA) (no. L-1400, lot no. 500481, Bachem Bioscience Inc., King of Prussia, Pa.) enzymatic substrate solution is prepared by dissolving 3.0 mg of SAAPFpNA per ml of 0.20M Tris buffer (Trizma Base, no. T-1503, lot no. 97F-5605, Sigma Chemical Co., St. Louis, Mo.) with 0.02% sodium azide, pH 7.6, or alternatively PBS. One drop of this solution (50 µl) at room temperature is then added to the filter surface and allowed to drain through.

4. A para-dimethylaminocinnamaldehyde (no. D-4506, lot no. 17F-0558, Sigma Chemical Co., St. Louis, Mo.) chemical enhancing reagent is prepared by adding 0.234 g of the para-dimethylaminocinnamaldehyde to 78 ml of ethanol, adding 10 ml of concentrated hydrochloric acid and making up to 100 ml with water. Three minutes after the application of the SAAPFpNA, 2 drops (100 µl) of this chemical enhancing reagent are then added to the filter surface and allowed to drain through. When positive for chymotrypsin-like activity, the area where the sample was spotted develops a reddish-purple color which varies in intensity with the amount of chymotrypsin-like activity present. An example of color development which is positive for the presence of chymotrypsin-like activity is presented in FIG. 1a. An example of a negative reaction for chymotrypsin-like activity is presented in FIG. 1b. The assay is usually completed in five minutes or less.

The assay does not have to be conducted precisely as specified. The pH, temperature, and concentrations of clinical and laboratory specimens and samples, enzymatic substrate, enhancing reagent or other reagents and reaction conditions may be varied. In a preferred commercial embodiment, the solid phase substrate flow-through filter devices are packaged with the materials, reagents and instructions necessary to perform the assay. When needed, a solid phase substrate filter device is removed from the packaging and a suspected protease-containing sample is placed on the filter surface of the device. The filter surface is then washed and an enzymatic substrate, such as SAAPFpNA, is applied followed a short time later by the addition of a chemical enhancing reagent, such as para-dimethylaminocinnamaldehyde, producing a detectable chromogenic reaction in the presence of protease activity. If certain levels of protease activity are present, e.g., chymotrypsin-like protease activity, a color will develop as shown in FIG. 1a.

ADVANTAGES AND NEW FEATURES

The invention can assist in screening patients for periodontal disease or assisting in the diagnostic process at specific sites within patients; monitoring patients or sites for risk of developing periodontal disease; planning treatment for periodontal disease; and monitoring patients or sites for the efficacy of periodontal treatment. Conventional clinical diagnostic and risk assessment methods are not normally based on bacterial profiles present in the mouth, only on subjective clinical signs which can be fraught with error. This invention removes much of this subjectivity and allows treatment decisions to be made on semi-quantitative data.

A unique aspect of this invention is its ability to rapidly and simply separate microbial proteases from host proteases. This is accomplished by using the filter surface on the solid phase substrate to trap microorganisms and their components while at the same time allowing other fluids, including those contributed by the host and possibly containing host proteases, to pass through. In so doing, the proteases that remain on the filter surface are primarily those contributed by the microorganisms.

In addition, this invention is rapid, inexpensive, simple to use and is easily performed by an auxiliary. The method is technically uncomplicated, sensitive, specific and semi-quantitative. The method can be used in a clinical setting with definitive results obtained while the patient is still in the chair—or even in a waiting room—thus allowing more rapid treatment decisions to be made.

PUBLICATIONS

1. Laughon, B. E., Syed, S. A. and Loesche, W. J. API ZYM system for identification of *Bacteroides* spp., *Capnocytophaga* spp., and spirochetes of oral origin. *J. Clin. Microbiol.* 15(1):97, 1982.

2. Uitto, V., Grenier, D., Chan, E. C. S. and McBride, B. C. Isolation of a chymotrypsinlike enzyme from *Treponema denticola*. *Infect. Immun.* 56(10):2717, 1988.

3. Grenier, D., Uitto, V. and McBride, B. C. Cellular location of a *Treponema denticola* chymotrypsinlike protease and importance of the protease in migration through the basement membrane. *Infect. Immun.* 58(2):347, 1990.

4. Loesche, W. J. The role of spirochetes in periodontal disease. *Adv. Dent. Res.* 2:275, 1988.

5. Ashley, F. P., Gallagher, J. and Wilson, R. F. The occurrence of *Actinobacillus actinomycetemcomitans, Bacteroides gingivalis, Bacteroides intermedius* and spirochetes in the subgingival microflora of adolescents and their relationship with the amount of supragingival plaque and gingivitis. *Oral Microbiol. Immunol.* 3:77, 1988.

6. Simonson, L. G., Goodman, C. H., Bial, J. J. and Morton, H. E. Quantitative relationship of *Treponema denticola* to severity of periodontal disease. *Infect. Immun.* 56:726, 1988.

7. Grenier, D. and Turgeon, J. Occurrence and identity of proteolytic bacteria in adult periodontitis. *J. Periodont. Res.* 29:365, 1994.

8. Loesche, W. J. The identification of bacteria associated with periodontal disease and dental caries by enzymatic methods. *Oral Microbiol. Immunol.* 1:65, 1986.

9. Pederson, E. D., Miller, J. W., Matheson, S., Simonson, L. G. et al. Trypsin-like activity levels of *Treponema denticola* and *Porphyromonas gingivalis* in adults with periodontitis. *J Clin. Periodontol.* 21(8):519, 1994.

10. Eley, B. M. and Cox, S. W. Cathespsin B/L, elastase-, tryptase-, trypsin-, and dipeptidyl peptidase IV-like activities in gingival crevicular fluid: a comparison of levels before and after periodontal surgery in chronic periodontitis patients. *J. Periodontol.* 63(5):412, 1992.

11. Cox, S. W. and Eley, B. M. Cathespsin B/L, elastase-, tryptase-, trypsin-, and dipeptidyl peptidase IV-like activities in gingival crevicular fluid. A comparison of levels before and after basic periodontal treatment of chronic periodontitis patients. *J. Clin. Periodontol.* 19(5):333, 1992.

12. Eley, B. M. and Cox, S. W. Correlation of gingival crevicular fluid proteases with clinical and radiological measurements of periodontal attachment loss. *J. Dent.* 20(2):90, 1992.

13. Loesche, W. J., Syed, S. A. and Stoll, J. Trypsin-like activity in subgingival plaque. A diagnostic marker for spirochetes and periodontal disease. *J. Periodontol.* 58(4):266, 1987.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

What is claimed is:

1. An assay means for rapidly detecting microbial protease activity in clinical and laboratory samples comprising:

a sample suspected of containing microorganisms having the desired protease activity and selected from the group consisting of dental plaque, saliva, oral rinse expectorant, urine, sweat, tears, blood, serum, stool, gastric fluid, synovial fluid, phlegm, culture media and other clinical and laboratory specimens and samples;

a flow-through solid phase substrate capable of immobilizing the desired microorganisms in the sample and allowing other fluids and materials which may contain host proteases to drain through;

an enzymatic substrate for application to the desired microorganisms immobilized on the solid phase substrate said enzymatic substrate capable of producing an enzymatic substrate end-product by interaction with said microorganism; and a chemical enhancing reagent capable of reacting with the enzymatic substrate end-product to produce a detectable chromogenic reaction.

2. The assay means of claim 1 wherein the enzymatic substrate is selected from the group consisting of para-nitroanilide peptide substrates and para-nitroanilide amino acid substrates for microbial proteases.

3. The assay means of claim 2 wherein the microbial protease is selected from the group consisting of microbial proteases which react with para-nitroanilide peptide substrates and para-nitroanilide amino acid substrates.

4. The assay means of claim 3 wherein the microbial protease is selected from the group consisting of chymotrypsin-like proteases; trypsin-like proteases; and collagenases.

5. A method of performing an assay for rapidly detecting microbial protease activity in clinical and laboratory samples comprising:

obtaining a sample suspected of containing microorganisms having the desired protease activity and selected from the group consisting of dental plaque, saliva, oral rinse expectorant, urine, sweat, tears, blood, serum, stool, gastric fluid, synovial fluid, phlegm, culture media and other clinical and laboratory specimens and samples;

contacting the sample with a solid phase substrate capable of immobilizing the desired microorganisms while allowing other fluids and materials which may contain host proteases to drain through;

contacting the desired microorganisms immobilized on the solid phase substrate with an enzymatic substrate to form an enzymatic substrate end-product;

contacting the enzymatic substrate end-product with a chemical enhancing reagent to produce a chromogenic reaction or signal; and detecting the chromogenic reaction or signal.

6. The assay method of claim 5 wherein the enzymatic substrate is selected from the group consisting of para-nitroanilide peptide substrates and para-nitroanilide amino acid substrates for microbial proteases.

7. The assay method of claim 6 wherein the microbial protease is selected from the group consisting of microbial proteases which react with para-nitroanilide peptide substrates and para-nitroanilide amino acid substrates.

8. The assay method of claim 7 wherein the microbial protease is selected from the group consisting of chymotrypsin-like proteases; trypsin-like proteases; and collagenases.

* * * * *